(12) United States Patent
Salamone et al.

(10) Patent No.: US 7,132,494 B2
(45) Date of Patent: Nov. 7, 2006

(54) HIGH REFRACTIVE INDEX AROMATIC-BASED SILYL MONOMERS

(75) Inventors: Joseph C. Salamone, Boca Raton, FL (US); Jay F. Kunzler, Canadaigua, NY (US); Richard M. Ozark, Solvay, NY (US); David E. Seelye, North Chili, NY (US); David P. Vanderbilt, Webster, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 10/848,305

(22) Filed: May 18, 2004

(65) Prior Publication Data

US 2004/0215156 A1 Oct. 28, 2004

Related U.S. Application Data

(62) Division of application No. 10/003,616, filed on Nov. 2, 2001, now Pat. No. 6,762,271.

(51) Int. Cl.
*C08G 77/00* (2006.01)

(52) U.S. Cl. .................. 528/43; 528/32; 556/437
(58) Field of Classification Search ............ 528/43, 528/32; 556/437
See application file for complete search history.

(56) References Cited

U.S. PATENT DOCUMENTS

| 3,996,187 A | 12/1976 | Travnicek | 260/37 |
|---|---|---|---|
| 3,996,189 A | 12/1976 | Travnicek | 260/37 |
| 4,418,165 A | 11/1983 | Polmanteer et al. | 523/210 |
| 4,647,282 A | 3/1987 | Fedorov et al. | 623/4 |
| 4,868,251 A | 9/1989 | Reich et al. | 525/479 |
| 5,512,609 A | 4/1996 | Yang | 523/107 |
| 5,623,029 A | 4/1997 | Yang | 525/478 |
| 5,700,874 A * | 12/1997 | Takeichi et al. | 525/288 |
| 5,760,019 A * | 6/1998 | Sieburth et al. | 514/63 |

FOREIGN PATENT DOCUMENTS

| EP | 413 465 | * | 2/1991 |
|---|---|---|---|
| JP | 61-294432 | * | 12/1986 |
| JP | 07-292283 | * | 11/1995 |

OTHER PUBLICATIONS

Sultanov et al., "Hydrosilylation of vinyl glycidyl ether", Zhurnal Obshchei Khimii (1969), 39(2), 396-397.*
Ushakov et al., Izvestiya Akademii Nauk SSSR, Seriya Khimicheskaya (1991), 5, 1207-1209.*
Wei et al., Journal of Organic Chemistry, (1989), 54, 5768-5774.*
Itami et al., Organic Letters, (2000) 2(9), 1299-1302.*
Morrison, "Orgqanic Chemistry", 3$^{rd}$ Ed., Allyn and Bacon, Inc., (1973) pp. 327-331.*
Volkova et al., "Synthesis of dimethylorgano(alpha-hydroxybutyl)silanes and diemthylorgano(delta-vinyloxybutyl)silanes", Zhurnal Obshchei Khimii (1980), 50(5), 1067-1071.*
Annenkova et al., "Polymerization and copolymerization of silicon-containing vinyl ethers", Vysokomolekulyamye Soedineniya, Seriya A (1973), 15(3), 560-563.*

* cited by examiner

*Primary Examiner*—Kuo-Liang Peng
(74) *Attorney, Agent, or Firm*—Toan P. Vo

(57) ABSTRACT

Optically transparent, relatively high refractive index polymeric compositions and ophthalmic devices such as intraocular lenses, contact lenses and corneal inlays made therefrom are described herein. The preferred polymeric compositions are produced through the polymerization of one or more aromatic-based silyl monomers or the copolymerization of one or more aromatic-based silyl monomers with one or more aromatic or non-aromatic non-siloxy-based monomers, hydrophobic monomers or hydrophilic monomers.

3 Claims, No Drawings

HIGH REFRACTIVE INDEX AROMATIC-BASED SILYL MONOMERS

This patent application is a divisional application of U.S. Patent Application having Ser. No. 10/003,616, filed on Nov. 2, 2001, now U.S. Pat. No. 6,762,271.

FIELD OF THE INVENTION

The present invention relates to monomers useful in the manufacture, of biocompatible medical devices. More particularly, the present invention relates to aromatic-based silyl monomers capable of polymerization alone or copolymerization with other monomers. Upon polymerization or copolymerization, the subject monomers form polymeric compositions having desirable physical characteristics and refractive indices useful in the manufacture of ophthalmic devices.

BACKGROUND OF THE INVENTION

Since the 1940's ophthalmic devices in the form of intraocular lens (IOL) implants have been utilized as replacements for diseased or damaged natural ocular lenses. In most cases, an intraocular lens is implanted within an eye at the time of surgically removing the diseased or damaged natural lens, such as for example, in the case of cataracts. For decades, the preferred material for fabricating such intraocular lens implants was poly(methyl methacrylate), which is a rigid, glassy polymer.

Softer, more flexible IOL implants have gained in popularity in more recent years due to their ability to be compressed, folded, rolled or otherwise deformed. Such softer IOL implants may be deformed prior to insertion thereof through an incision in the cornea of an eye. Following insertion of the IOL in an eye, the IOL returns to its original pre-deformed shape due to the memory characteristics of the soft material. Softer, more flexible IOL implants as just described may be implanted into an eye through an incision that is much smaller, i.e., less than 4.0 mm, than that necessary for more rigid IOLs, i.e., 5.5 to 7.0 mm. A larger incision is necessary for more rigid IOL implants because the lens must be inserted through an incision in the cornea slightly larger than the diameter of the inflexible IOL optic portion. Accordingly, more rigid IOL implants have become less popular in the market since larger incisions have been found to be associated with an increased incidence of postoperative complications, such as induced astigmatism.

With recent advances in small-incision cataract surgery, increased emphasis has been placed on developing soft, foldable materials suitable for use in artificial IOL implants. In general, the materials of current commercial IOLs fall into one of three general categories: silicones, hydrophilic acrylics and hydrophobic acrylics.

In general, high water content hydrophilic acrylics, or "hydrogels," have relatively low refractive indices, making them less desirable than other materials with respect to minimal incision size. Low refractive index materials require a thicker IOL optic portion to achieve a given refractive power. Silicone materials may have a higher refractive index than high-water content hydrogels, but tend to unfold explosively after being placed in the eye in a folded position. Explosive unfolding can potentially damage the corneal endothelium and/or rupture the natural lens capsule and associated zonules. Low glass transition temperature hydrophobic acrylic materials are desirable because they typically have a high refractive index and unfold more slowly and more controllably than silicone materials. Unfortunately, low glass transition temperature hydrophobic acrylic materials, which contain little or no water initially, may absorb pockets of water in vivo causing light reflections or "glistenings." Furthermore, it may be difficult to achieve ideal folding and unfolding characteristics due to the temperature sensitivity of some acrylic polymers.

Because of the noted shortcomings of current polymeric materials available for use in the manufacture of ophthalmic implants, there is a need for stable, biocompatible polymeric materials having desirable physical characteristics and refractive indices.

SUMMARY OF THE INVENTION

Soft, foldable, high refractive index, high elongation polymeric compositions of the present invention are produced through the polymerization or copolymerization of aromatic-based silyl monomers. The subject monomers are synthesized through a multi-step reaction scheme. The polymeric compositions produced from the silyl monomers have ideal physical properties for the manufacture of ophthalmic devices. The polymeric compositions of the present invention are transparent, of relatively high strength for durability during surgical manipulations, of relatively high elongation, of relatively high refractive index and are biocompatible. The subject polymeric compositions are particularly well suited for use as intraocular lens (IOLs) implants, contact lenses, keratoprostheses, corneal rings, corneal inlays and the like.

Preferred aromatic-based silyl monomers for use in preparing the polymeric compositions of present invention have the generalized structure represented by Formula 1 below,

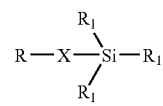

Formula 1 wherein R is a polymerizable group; X is selected from the group consisting of $C_{1-10}$ alkylene, $C_{1-10}$ alkyleneoxy, $C_{6-36}$ arylene, and $C_{6-36}$ aryleneoxy; and the $R_1$ groups may be the same or different selected from the group consisting of $C_{1-10}$ alkyl, $C_{1-20}$ cycloalkyl, $C_{6-36}$ aryl, $C_{6-36}$ aryl ether, $C_{6-36}$ heterocycle, $C_{6-36}$ heterocycle with one or more substituents, $C_{1-10}$ alkyl ether and $C_{6-36}$ aryloxy.

Accordingly, it is an object of the present invention to provide transparent, polymeric compositions having desirable physical characteristics for the manufacture of ophthalmic devices.

Another object of the present invention is to provide polymeric compositions of relatively high refractive index.

Another object of the present invention is to provide polymeric compositions suitable for use in the manufacture of intraocular lens implants.

Another object of the present invention is to provide polymeric compositions that are biocompatible.

Another object of the present invention is to provide polymeric compositions suitable for use as contact lens materials.

Still another object of the present invention is to provide polymeric compositions that are economical to produce.

These and other objectives and advantages of the present invention, some of which are specifically described and others that are not, will become apparent from the detailed description and claims that follow.

DETAILED DESCRIPTION OF THE INVENTION

The present invention relates to novel aromatic-based silyl monomers synthesized through a three-step reaction scheme. The subject aromatic-based silyl monomers are useful in the production of biocompatible polymeric compositions. The subject polymeric compositions have particularly desirable physical properties. The subject polymeric compositions have a relatively high refractive index of approximately 1.45 or greater and relatively high elongation of approximately 100 percent or greater. Accordingly, the subject polymeric compositions are ideal for use in the manufacture of ophthalmic devices. The aromatic-based silyl monomers of the present invention are generally represented by Formula 1 below:

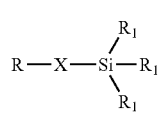

Formula 1 wherein R is a polymerizable group selected from the group consisting of methacrylate, acrylate, acrylamido, methacrylamido, styryl, itaconate, fumaroyl, vinyl, vinyloxy, vinyl carbamate and vinyl carbonate; X is selected from the group consisting of $C_{1-10}$ alkylene, such as for example but not limited to methylene, trimethylene or heptamethylene, $C_{1-10}$ alkyleneoxy, such as for example but not limited to ethyleneoxy, butyleneoxy or octyleneoxy, $C_{6-36}$ arylene, such as for example but not limited to phenylene or naphthylene and $C_{6-36}$ aryleneoxy, such as for example but not limited to phenyleneoxy or naphthyleneoxy; and the $R_1$ groups may be the same or different selected from the group consisting of $C_{1-10}$ alkyl such as for example but not limited to methyl, propyl or pentyl but preferably propyl for increased stability, $C_{1-20}$ cycloalkyl such as for example but not limited to cyclohexyl or cycloheptyl, $C_{6-36}$ aryl such as for example but not limited to phenyl or naphthyl, $C_{6-36}$ aryl ether such as for example but not limited to phenyl ether or naphthyl ether, $C_{6-36}$ heterocycle such as for example but not limited to pyridine, quinoline, furan or thiophene but preferably pyridine to increase refractive index, $C_{6-36}$ heterocycle such as those described above with one or more substituents such as for example but not limited to chlorine, fluorine, amine, amide, ketone or $C_{1-3}$ alkyl such as for example methyl or propyl, $C_{6-36}$ aryloxy such as for example but not limited to phenyloxy or naphthyloxy and $C_{1-10}$ alkyl ethers such as for example methyl ether or propyl ether.

Examples of aromatic-based silyl monomers of the present invention include for example but are not limited to 1-methacryloyloxypropyldimethylphenylsilane, 1-methacryloyloxypropyldiphenylmethylsilane and 1-methacryloyloxypropyltriphenylsilane.

Aromatic-based silyl monomers of the present invention may be synthesized through a three-step reaction scheme as represented in Scheme 1 below:

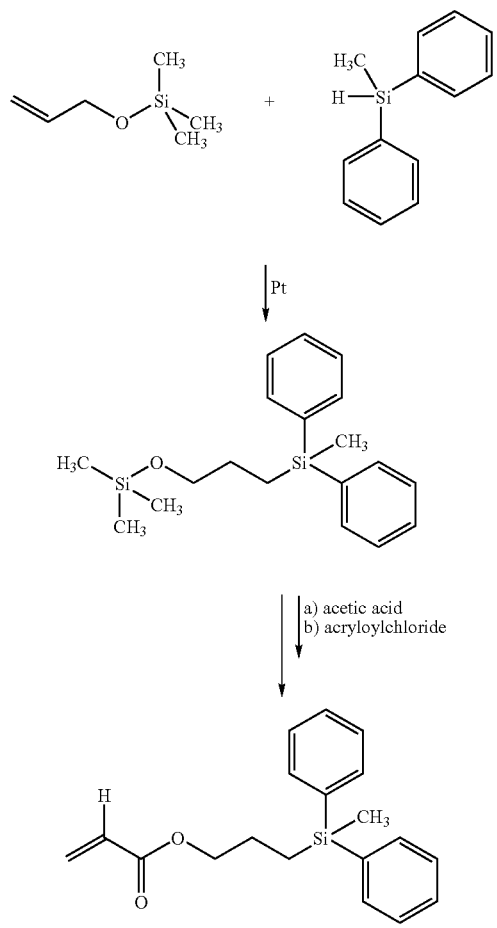

One or more aromatic-based silyl monomers of the present invention produced as described above may be polymerized alone or copolymerized with other monomers. One or more of the subject silyl monomers may be copolymerized with one or more aromatic or non-aromatic non-siloxy-based monomers, hydrophobic monomers, hydrophilic monomers or a combination thereof to produce polymeric compositions of the present invention.

Examples of aromatic and non-aromatic non-siloxy-based monomers useful for copolymerization with one or more aromatic-based silyl monomers of the present invention include for example but are not limited to 2-phenoxyethyl methacrylate, 3,3-diphenylpropyl methacrylate, N,N-dimethylacrylamide, methyl methacrylate, 2-(1-naphthylethyl) methacrylate, glycol methacrylate, 3-phenylpropyl acrylate and 2-(2-naphthylethyl) methacrylate but preferably 2-(1-naphthylethyl) methacrylate for increased refractive index.

Examples of hydrophobic monomers useful for copolymerization with one or more aromatic-based silyl monomers of the present invention include for example but are not limited to 2-ethylhexyl methacrylate, 3-methacryloyloxypropyldiphenylmethylsilane and 2-phenoxyethyl methacrylate but preferably 3-methacryloyloxypropyldiphenylmethylsilane for increased refractive index.

Examples of hydrophilic monomers useful for copolymerization with one or more aromatic-based silyl monomers of the present invention include for example but are not limited to N,N-dimethylacrylamide and methyl methacrylate but preferably N,N-dimethylacrylamide for increased hydrophilicity.

The physical and mechanical properties of copolymers produced from formulations based on 3-phenylpropyl acrylate (PPA), N,N-dimethylacrylamide (DMA), 3-acryloyloxypropyldiphenylmethylsilane (APDMS) and methyl methacrylate (MMA) with are set forth below in Table 1.

TABLE 1

Mechanical and Physical Property Results of formulations based on PPA, DMA and APDMS (initiator Irgacure™ 819 at 0.5% (Ciba-Geigy, Basel, Switzerland) and UV blocker at 0.25% for all formulations)

| Composition | W/W % | R.I. | Mod (g/mm$^2$) | Tear (g/mm) | % Elong. | % Rec. | % H$_2$O |
|---|---|---|---|---|---|---|---|
| PPA/DMA/APDMS/Hex/Eg/819 | 75/25/0/20/1 | 1.5349 | | | | | 5.1 |
| | 75/25/0/20/2 | 1.5364 | 55 | 24 | 197 | 88 | 6.5 |
| | 75/25/0/20/3 | | | | | 86 | 5.0 |
| | 65/25/10/20/1 | 1.5396 | 50 | 47 | 338 | 80 | 4.5 |
| | 65/25/10/20/2 | 1.5442 | 81 | 54 | 228 | 77 | 5 |
| | 65/25/10/20/3 | 1.5448 | 143 | 57 | 178 | 72 | 5.7 |
| | 55/25/20/20/1 | 1.5409 | 94 | 79 | 332 | 70 | 5.5 |
| | 55/25/20/20/2 | 1.5429 | 141 | 77 | 232 | 64 | 4.8 |
| | 55/25/20/20/3 | 1.5422 | 196 | 83 | 184 | 60 | 5 |

Hex = Hexanol
Eg = EGDMA = Ethyleneglycol dimethacrylate
819 = Irgacure™ 819

No water content, low water content of less than 15 percent water content by volume and high water content "hydrogels" of 15 percent or higher water content by volume polymeric compositions of the present invention having ideal physical characteristics for use in the manufacture of ophthalmic devices are described herein. In the production of such polymeric compositions of the present invention, one or more silyl monomers of the present invention may be polymerized or copolymerized to form crosslinked three-dimensional networks. However, one or more crosslinking agents may be added in quantities less than 10 percent weight per volume (W/V) to the silyl monomer(s), if desired, prior to polymerization or copolymerization thereof.

Examples of suitable crosslinking agents include but are not limited to diacrylates and dimethacrylates of triethylene glycol, butylene glycol, neopentyl glycol, hexane-1,6-diol, thio-diethylene glycol and ethylene glycol, trimethylolpropane triacrylate, N,N'-dihydroxyethylene bisacrylamide, diallyl phthalate, triallyl cyanurate, divinylbenzene; ethylene glycol divinyl ether, N,N'-methylene-bis-(meth)acrylamide, sulfonated divinylbenzene and divinylsulfone.

Although not required, silyl monomers within the scope of the present invention may optionally have one or more strengthening agents added thereto prior to polymerization or copolymerization thereof, preferably in quantities of less than about 80 weight percent but more typically from about 20 to about 60 weight percent.

Examples of suitable strengthening agents are described in U.S. Pat. Nos. 4,327,203, 4,355,147 and 5,270,418, each incorporated herein in its entirety by reference. Specific examples, not intended to be limiting, of such strengthening agents include cycloalkyl acrylates and methacrylates, such as for example tert-butylcyclohexyl methacrylate and isopropylcyclopentyl acrylate.

One or more ultraviolet light absorbers may optionally be added to the subject silyl monomers prior to polymerization or copolymerization thereof in quantities typically less than 2 percent W/V. Suitable ultraviolet light absorbers for use in the present invention include for example but are not limited to β-(4-benzotriazoyl-3-hydroxyphenoxy)ethyl acrylate, 4-(2-acryloyloxyethoxy)-2-hydroxybenzophenone, 4-methacryloyloxy-2-hydroxybenzophenone, 2-(2'-methacryloyloxy-5'-methylphenyl)benzotriazole, 2-(2'-hydroxy-5'-methacryloyloxyethylphenyl)-2H-benzotriazole, 2-[3'-tert-butyl-2'-hydroxy-5'-(3''-methacryloyloxypropyl)phenyl]-5-chlorobenzotriazole, 2-(3'-tert-butyl-5'-(3''-dimethylvinylsilylpropoxy)-2'-hydroxyphenyl]-5-methoxybenzotriazole, 2-(3'-allyl-2'-hydroxy-5'-methylphenyl)benzotriazole, 2-[3'-tert-butyl-2'-hydroxy-5'-(3''-methacryloyloxypropoxy)phenyl]-5-methoxybenzotriazole, and 2-[3'-tert-butyl-2'-hydroxy-5'-(3''-methacyloyloxypropoxy)phenyl]-5-chlorobenzotriazole wherein β-(4-benzotriazoyl-3-hydroxyphenoxy)ethyl acrylate is the preferred ultraviolet light absorber.

The silyl monomers of the present invention may be readily cured in cast shapes, as discussed in more detail below, by one or more conventional methods. Such methods include for example but are not limited to ultraviolet light polymerization, visible light polymerization, microwave polymerization, thermal polymerization, free radical thermal polymerization or combinations thereof.

One or more suitable free radical thermal polymerization initiators may be added to the monomers of the present invention. Examples of such initiators include for example but are not limited to organic peroxides, such as acetyl peroxide, lauroyl peroxide, decanoyl peroxide, stearoyl peroxide, benzoyl peroxide, tert-butyl peroxypivalate, peroxydicarbonate, and the like. Preferably such an initiator is employed in a concentration of approximately 0.01 to 1 percent by weight of the total monomer mixture.

Representative ultraviolet light initiators include those known in the field such as for example but not limited to benzoin methyl ether, benzoin ethyl ether, Darocur™ 1173, 1164, 2273, 1116, 2959, 3331 (EM Industries) and Irgacur™ 651 and 184 (Ciba-Geigy, Basel, Switzerland).

The polymeric compositions of the present invention are of relatively high refractive index, relatively high elongation and relatively high clarity. The polymeric compositions of the present invention with the desirable physical properties noted above are particularly useful in the manufacture of ophthalmic devices such as but not limited to relatively thin, foldable intraocular lens implants, contact lenses and corneal inlays.

IOLs having relatively thin optic portions are critical in enabling a surgeon to minimize surgical incision size. Keeping the surgical incision size to a minimum reduces intra-operative trauma and postoperative complications. A relatively thin IOL optic portion is also critical for accommodating certain anatomical locations in the eye such as the anterior chamber and the ciliary sulcus. IOLs may be placed in the anterior chamber for increasing visual acuity in either aphakic or phakic eyes, or placed in the ciliary sulcus for increasing visual acuity in phakic eyes.

The polymeric compositions of the present invention have the flexibility required to allow implants manufactured from the same to be folded or deformed for insertion into an eye through the smallest possible surgical incision, i.e., 3.5 mm or smaller. It is unexpected that the subject polymeric compositions could possess the ideal physical properties described herein. The ideal physical properties of the subject polymeric compositions are unexpected because high refractive index monomers typically lend to polymers that have increased crystallinity and decreased clarity, which does not hold true in the case of the subject polymeric compositions.

The subject silyl monomers and polymeric compositions produced therefrom are described in still greater detail in the examples that follow.

EXAMPLE 1

Three-step Synthesis of
3-acryloyloxypropydiphenyl-methylsilane (APDMS)

Step one: Synthesis of
3-(trimethylsilyloxy)propyldiphenylmethylsilane

In a two liter acid washed round bottom flask equipped with magnesium stirrer, condenser and dry air tube was placed 100 g of diphenylmethylsilane, (0.5042 moles), 656.7 g of trimethylsilylallyl (TMS-allyl) alcohol (5.042 moles) and 1000 µl of Pt catalyst (Aldrich Chemical Co. 47,951-9). The solution was refluxed for 16 hours, cooled to room temperature and 20g of silica gel was added. Stirring was continued for 2 hours. The mixture was filtered and rotovapped to oil. The oil was vacuum distilled (boiling point (b.p.) 110–15° C. at 0.1 mm Hg). Recovered 158 g (GC-97%) yield 95%.

Step two: Synthesis of
3-hydroxypropyldiphenylmethylsilane

In a one liter erylenmeyer flask was placed 161 g of the product from step one above (0.4901 mole) dissolved in 700 ml of methanol. To the above was slowly added 35 ml of distilled water followed by 4 ml of glacial acetic acid. This solution was stirred for 2 hours. The solution was rotovapped to remove the methanol; re-dissolved in chloroform, washed with distilled water three times, dried over magnesium sulfate and filtered. The solution was rotovapped to a clear oil. Recovered 132 g (GC purity 93%).

Step three: Synthesis of
3-acryloyloxypropyldiphenylmethylsilane

In a two liter round bottom flask equipped with mechanical stirrer, dropping funnel, thermometer, condenser and $N_2$ blanket was placed 132 g (0.4758 mole) of the deprotected alcohol, 53.6 g (0.53 moles) of triethylamine and 1000 ml of anhydrous ethyl acetate. This solution was cooled to 0° C. and 47g (0.5234 moles) of acryloyl chloride was added dropwise, keeping the temperature less than 5° C. After the addition was complete, the reaction was allowed to come to room temperature and stirred under $N_2$ overnight. The next morning the solution was washed three times with cold 2N HCl, one time with brine and one time with 5% $NaHCO_3$. The resulting solution was dried over $MgSO_4$, filtered and rotovapped to a yellow oil. The oil was passed through a 400 g silica column eluding with 70/30, 50/50 and 30/70 heptane/dichloromethane solutions (2 bed volumes each). After solvent removal, 59 g of 3-acryloyloxypropyldiphenylmethylsilane (98.6% by GC) was recovered.

Synthesis of 2-(1-napthalylethyl) Methacrylate

In a two liter amber colored round bottom flask equipped with mechanical stirrer, dropping funnel, thermometer, condenser, and $N_2$ blanket was placed 50 g (0.2905 mole) of 1-naphthaleneethanol, 31.4 g (0.31 mole) of triethylamine and 1000 ml of ethyl acetate. The above was cooled to less than 0° C. and 31.9 g (0.305 mole) of methacryloyl chloride was added dropwise keeping the temperature less than 0° C. The reaction was allowed to come to room temperature and stirred under $N_2$ overnight. The following morning, the organic layer was washed two times with 1N HCl, one time with brine, and two times with 5% $NaHCO_3$. The organic layer was dried over $MgSO_4$, filtered and rotovapped to an oil, and passed through 200 g of silica gel eluding with 70/30 heptane/dichloromethane. After solvent removal, recovered 48 g (GC purity 97%).

EXAMPLE 2

To 65 parts of 3-phenylpropyl acrylate (PPA) was added 25 parts of N,N-dimethylacrylamide, 20 parts of hexanol, 10 parts of APDMS, 3 parts of ethyleneglycol dimethacrylate and 0.5% of Irgacure™ 819 as the UV photoinitiator and 0.25% of a commercial triazole UV blocker (Aldrich Chemical Co). The clear solution was sandwiched between two silanized glass plates using metal gaskets and exposed to UV radiation for two hours. The resultant films were released and extracted in isopropanol (IPA) for four hours, followed by air-drying and a 30 mm vacuum to remove the IPA. The resultant film was hydrated at room temperature overnight in borate buffered saline. The clear tack-free films possessed a modulus of 81 g/mm$^2$, a tear strength of 77 g/mm, a % elongation of 228%, a water content of 5% and a refractive index of 1.5442.

EXAMPLE 3

To 70 parts of APDMS was added 10 parts of N,N-dimethylacrylamide, 20 parts of hexanol, 1 part of ethyleneglycol dimethacrylate and 0.5% of Irgacure™ 819 as the UV photoinitiator and 0.25% of a commercial triazole UV blocker (Aldrich Chemical Co). The clear solution was sandwiched between two silanized glass plates using metal gaskets and exposed to UV radiation for two hours. The resultant films were released and extracted in IPA for four hours, followed by air-drying and a 30 mm vacuum to remove the IPA. The resultant film was hydrated at room temperature overnight in borate buffered saline. The clear tack-free films possessed a modulus of 161 g/mm$^2$, a tear strength of 64 g/mm, a % elongation of 183%, a water content of 10.5% and a refractive index of 1.517.

Ophthalmic devices such as but not limited to IOLs manufactured using the polymeric compositions of the present invention can be of any design capable of being rolled or folded for implantation through a relatively small surgical incision, i.e., 3.5 mm or less. For example, ophthalmic devices such as IOLs typically comprise an optic portion and one or more haptic portions. The optic portion reflects light onto the retina and the permanently attached haptic portions hold the optic portion in proper alignment within an eye. The haptic portions may be integrally formed with the optic portion in a one-piece design or attached by staking, adhesives or other methods known to those skilled in the art in a multipiece design.

The subject ophthalmic devices, such as for example IOLs, may be manufactured to have an optic portion and haptic portions made of the same or differing materials. Preferably, in accordance with the present invention, both the optic portion and the haptic portions of the IOLs are made of one or more polymeric compositions of the present invention. Alternatively however, the IOL optic portion and haptic portions may be manufactured from differing materials and/or differing polymeric compositions of the present invention, such as described in U.S. Pat. Nos. 5,217,491 and 5,326,506, each incorporated herein in its entirety by reference. Once the particular material or materials are selected, the same is either cast in molds of the desired shape or cast in the form of rods and lathed or machined into disks. If cast in the form of rods and lathed or machined into disks, the disks are lathed or machined into IOLs at low temperatures below the glass transition temperature(s) of the material(s). The IOLs, whether molded or machined/lathed, are then cleaned, polished, packaged and sterilized by customary methods known to those skilled in the art.

In addition to IOLs, the polymeric compositions of the present invention are also suitable for use in the manufacture of other ophthalmic devices such as but not limited to contact lenses, keratoprostheses, capsular bag extension rings, corneal inlays, corneal rings or like devices.

IOLs manufactured using the unique polymeric compositions of the present invention are used as customary in the field of ophthalmology. For example, in a surgical procedure, an incision is placed in the cornea of an eye. Most commonly, through the corneal incision the natural lens of the eye is removed (aphakic application) such as in the case of a cataractous natural lens. An IOL is then inserted into the anterior chamber, posterior chamber or lens capsule of the eye prior to closing the incision. However, the subject ophthalmic devices may be used in accordance with other surgical procedures known to those skilled in the field of ophthalmology.

While there is shown and described herein monomers and polymeric compositions, methods of producing the monomers and polymeric compositions, methods of producing ophthalmic devices using the polymeric compositions and methods of using ophthalmic devices manufactured from the polymeric compositions, all in accordance with the present invention, it will be manifest to those skilled in the art that various modifications may be made without departing from the spirit and scope of the underlying inventive concept. The present invention is likewise not intended to be limited to particular devices described herein except insofar as indicated by the scope of the appended claims.

We claim:

1. Aromatic-based silyl monomers having a structure represented by

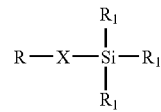

wherein R is a polymerizable group selected from the group consisting of acrylamido, methacrylamido, itaconate, fumaroyl, vinyl carbamate, and vinyl carbonate; X is selected from the group consisting of $C_{1-10}$ alkylene, $C_{6-36}$ alkyleneoxy, $C_{6-36}$ arylene, and $C_{6-36}$ aryleneoxy; and the $R_1$ groups are the same or different, and are selected from the group consisting of $C_{1-10}$ alkyl, $C_{1-20}$ cycloalkyl, $C_{6-36}$ aryl, $C_{6-36}$ aryl ether, $C_{6-36}$ heterocycle, $C_{6-36}$ heterocycle with one or more substituents, $C_{1-10}$ alkyl ether and $C_{6-36}$ aryloxy, with at least one $R_1$ group being other than a methyl group and at least one $R_1$ group being non-phenyl and at least one $R_1$ group being an aromatic-based group.

2. Aromatic-based silyl monomers having a structure represented by

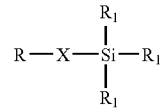

wherein R is a polymerizable group selected from the group consisting of acrylamido, methacrylamido, itaconate, fumaroyl, vinyl carbamate, and vinyl carbonate; X is selected from the group consisting of $C_{1-10}$ alkylene, $C_{1-10}$ alkyleneoxy, $C_{6-36}$ arylene, and $C_{6-36}$ aryleneoxy; and the $R_1$ groups are the same or different, and are selected from the group consisting of $C_{1-10}$ alkyl, $C_{1-20}$ cycloalkyl, naphthyl, $C_{6-36}$ aryl ether, $C_{6-36}$ heterocycle, $C_{6-36}$ heterocycle with one or more substituents, $C_{1-10}$ alkyl ether and $C_{6-36}$ aryloxy; and at least one $R_1$ group being an aromatic-based group.

3. Aromatic-based silyl monomers having a structure represented by

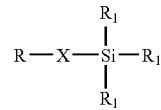

wherein R is a polymerizable group selected from the group consisting of acrylamido, methacrylamido, itaconate, fumaroyl, vinyl carbamate, and vinyl carbonate; X is selected from the group consisting of $C_{1-10}$ alkylene, $C_{1-10}$ alkyleneoxy, $C_{6-36}$ arylene, and $C_{6-36}$ aryleneoxy; and the $R_1$ groups are different and are selected from the group consisting of $C_{1-20}$ cycloalkyl, $C_{6-36}$ aryl, $C_{6-36}$ aryl ether, $C_{6-36}$ heterocycle, $C_{6-36}$ heterocycle with one or more substituents, $C_{1-10}$ alkyl ether and $C_{6-36}$ aryloxy; and at least one $R_1$ group being an aromatic-based group.

* * * * *

UNITED STATES PATENT AND TRADEMARK OFFICE
CERTIFICATE OF CORRECTION

PATENT NO. : 7,132,494 B2  Page 1 of 1
APPLICATION NO. : 10/848305
DATED : November 7, 2006
INVENTOR(S) : Salamone et al.

It is certified that error appears in the above-identified patent and that said Letters Patent is hereby corrected as shown below:

In Col. 10, line 14 replace "$C_{6-36}$ alkyle-"

with "$C_{1-10}$ alkyle-".

Signed and Sealed this

Sixteenth Day of March, 2010

David J. Kappos
*Director of the United States Patent and Trademark Office*